United States Patent
Nagabhushanam et al.

(10) Patent No.: US 10,071,043 B2
(45) Date of Patent: Sep. 11, 2018

(54) OLEANOYL PEPTIDE COMPOSITION AND SKIN HYDRATION

(71) Applicants: Kalyanam Nagabhushanam, East Windsor, NJ (US); Muhammed Majeed, Edison, NJ (US)

(72) Inventors: Kalyanam Nagabhushanam, East Windsor, NJ (US); Muhammed Majeed, Edison, NJ (US)

(73) Assignee: SAMI LABS LIMITED, Bangalore (IN)

( * ) Notice: Subject to any disclaimer, the term of this patent is extended or adjusted under 35 U.S.C. 154(b) by 122 days.

(21) Appl. No.: 14/983,874

(22) Filed: Dec. 30, 2015

(65) Prior Publication Data

US 2016/0113853 A1   Apr. 28, 2016

Related U.S. Application Data

(60) Division of application No. 14/614,538, filed on Feb. 5, 2015, now abandoned, which is a continuation-in-part of application No. 12/979,667, filed on Dec. 28, 2010, now Pat. No. 8,987,212, which is a continuation-in-part of application No. 11/835,165, filed on Aug. 7, 2007, now Pat. No. 8,383,594.

(51) Int. Cl.
*A61K 8/64* (2006.01)
*A61Q 19/00* (2006.01)
*A61Q 19/08* (2006.01)
*C07K 7/06* (2006.01)
*A61Q 19/04* (2006.01)

(52) U.S. Cl.
CPC ............ *A61K 8/64* (2013.01); *A61Q 19/00* (2013.01); *A61Q 19/007* (2013.01); *A61Q 19/04* (2013.01); *A61Q 19/08* (2013.01); *C07K 7/06* (2013.01); *A61K 2800/57* (2013.01); *A61K 2800/78* (2013.01)

(58) Field of Classification Search
None
See application file for complete search history.

(56) References Cited

U.S. PATENT DOCUMENTS

2010/0034758 A1* 2/2010 Majeed .................... A61K 8/64
424/59

OTHER PUBLICATIONS

Boury-Jamot et al. ('Expression and function of aquaporins in human skin: Is aquaporin-3 just a glycerol transporter?' Biochemica et Biophysica Acta v1758 2006 pp. 1034-1042).*
Pereda et al. ('Expression of differential genes involved in the maintenance of water balance in human skin by Piptadenia colubrina extract' Journal of Cosmetic Dermatology v9 2010 pp. 35-43).*
M. Boury-Jamot et al, "Expression and function of aquaporins in human skin: Is aquaporin-3 just a glycerol transporter?", Biochimica et Biophysica Acta 1758 (2006) 1034-1042.
A. S. Verkman, "More than just water channels: unexpected cellular of aquaporins", Journal of Cell Science 118, 3225-3232 Published by The Company of Biologists 2005.
Rawlings, A. V. and Harding, C. R. (2004), Moisturization and skin barrier function. Dermatologic Therapy, 17: 43-48. doi: 10.1111/j.1396-0296.2004.04S1005.x.
Yuanlin Song et al, "Localisation of aquaporin-5 in sweat glands and functional analysis using knockout mice", Journal of Physiology (2002), 541.2, pp. 561-568.

* cited by examiner

*Primary Examiner* — Karlheinz R. Skowronek
*Assistant Examiner* — Ronald T Niebauer (57) ABSTRACT

Disclosed is the a method of effecting skin hydration and enhancing skin barrier function, said method comprising the step of bringing into contact a pentapeptide conjugate of oleanolic acid with skin cells so that the effect of increased cellular communication at the molecular level to bring about gene and protein expression in the cells of the skin that enable hydration and skin barrier functions are realized.

3 Claims, 6 Drawing Sheets

Specification includes a Sequence Listing.

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence : Synthetic peptide

<400> SEQUENCE: 1

Lys Thr Thr Lys Ser
1               5

OLEANOYL PEPTIDE COMPOSITION AND SKIN HYDRATION

CROSS-REFERENCE TO RELATED APPLICATIONS

This application is a divisional application of U.S. Ser. No. 14/614,538 filed on Feb. 5, 2015 which in turn is a continuation-in-part of U.S. application Ser. No. 12/979,667 filed on 28 Dec. 2010 titled "OLEANOYL PEPTIDE COMPOSITION AND A METHOD OF TREATING SKIN AGING", which in-turn is a continuation-in-part of application Ser. No. 11/835,165 filed Aug. 7, 2007 titled "PEPTIDES MODIFIED WITH TRITERPENOIDS AND SMALL ORGANIC MOLECULES: SYNTHESIS AND USE IN COSMECEUTICALS" both of which are hereby incorporated by reference in their entirety for all purposes.

FIELD OF THE INVENTION

The present invention relates to a composition containing peptide of SEQ ID No. 1 linked to oleanolic acid and its use in a method of skin repair and firming by the regulation of associated gene expression.

BACKGROUND OF THE INVENTION

The appearance and condition of the skin may be degraded through the effects of environmental factors, either naturally occurring (sunlight, wind abrasion, humidity, etc) or man-made (heating, air condition, pollutants, etc), pathological processes such as dermatological diseases or the normal aging process. The various insults to which the skin is exposed may act individually or synergistically. To ameliorate or prevent the deterioration of skin quality that may occur over time, consumers have increasingly sought new or improved cosmetic compositions and cosmetic methods for skin care. Such products or methods prevent, delay or reverse the visible signs of the aging process, such as the appearance of wrinkles, lines, loss of skin tone, thinning, of the skin, hyper pigmentation or mottling and age spots. Such products or methods improve the appearance and condition of sensitive, dry or flaky skin, and/or soothe skin that has been irritated by exposure to chemicals, wind, or sunlight, among other potential irritants.

With an aging population, there has been an increase in the study of aging as it relates to the human body and, more particularly, human skin. For example, treatment of aging skin exhibited by the presence of fine lines, wrinkles and the like has received a great deal of attention. The dermal signs of aging such as fine lines, wrinkles, laxity, and hyperpigmentation have been fought through many tactics including surgery, laser treatment and cosmetics. Cosmetic treatments include use of various creams and lotions to alter the effects of dermal aging. Much of the literature in the prior art focuses on the use of a single primary component to prevent one of several deleterious aging affects. For example, one tactic has been to use one or more hydroxy acids or retinoic acid to stimulate the re-growth of dermal cells without other components. This approach is flawed because it does not recognize that aging is caused by the deleterious interaction of multiple agents on the skin, from multiple sources, causing damage to the skin through multiple simultaneous damage pathways.

Consumers are increasingly seeking "anti-aging" products that treat wrinkling, creasing and furrowing of the skin. The advent of costly and painful cosmetic injections for treating expression lines of the face has heightened interest in finding topical alternatives that are effective and non-invasive.

Expression lines are a distinct type of wrinkle that occurs on the facial skin at an early adult age. They are related anatomically to the facial expression muscles in the periorbital, glabella, forehead and perioral areas. The activity of these muscles during the actions of smiling, squinting, pursing of the lips and frowning places greater physical stress upon the overlying skin than in other areas in the face. For this reason, expression lines are less responsive to those topical treatments that focus upon the non-contractile elements of cutaneous anatomy, such as the epidermis. In order to be most effective, treatment of expression lines should also entail the inhibition of the facial expression muscles and the muscle fiber elements associated with the dermis. A myriad of substances that relax striated muscle fibers are described in the cosmetic prior art. The problem is that the muscle relaxants of the prior art are either slow acting, not potent enough or the inhibitory effects are not cumulative. Furthermore, none of these muscle relaxants reduce facial muscle actions. A newly discovered plant extract that rapidly inhibits deformation of the dermis enables substances that repair and rejuvenate if to become more effective.

An expression line is formed when a muscle of facial expression contracts or shortens itself beneath the skin and then relaxes and returns to its resting length. The skin can also shorten and rebound, but not as well as the muscle. Therefore, the skin tends to buckle and fold inward as the muscle contracts. The ability of the skin to withstand the shortening and rebounding of the underlying muscle is related to the quality and health of the upper dermis. With increasing age, the thickness, elasticity, collagen content and reparative ability of the dermis diminishes. The skin can no longer rebound from this action and the fibrous inter-cellular matrix of the dermis weakens and breaks. At this point, the skin has developed a permanent wrinkle. The wrinkle will continue to deepen as this area of the skin is subjected to the perpetual stress of facial expressions.

Anatomy of Expression Lines

The skin associated with expression lines is different histologically from that found elsewhere in the face. The interlobular septa of the sub-dermal connective tissue contain striated muscle tissue fibers (panniculus carnosus). These fibers arise from the underlying facial muscle groups. They are integrated within the collagenous network of the lower (reticular) dermis. A sub-population of dermal fibroblasts in the upper (papillary) dermis, known as "myofibroblasts", have inherent contractile characteristics similar to striated muscle tissue. Contractions within these dermal fibroblasts are mediated by the same neurotransmitter, i.e. acetylcholine, as the fiber elements of striated muscle.

Muscle fibers within the facial skin have a direct influence on its surface smoothness and modulating the neural motor influx to these muscle fibers causes a reduction of wrinkles. For example, patients who suffer from Bell's palsy of the facial nerve have smoother skin on the paralyzed side of the face than on the non-paralyzed side. Also, Botox™ Cosmetic injections not only immobilize the forehead and upper eyebrow muscles, but also smoothen the skin external to these muscles, Botox™ interferes with the uptake of acetylcholine within the synaptic junction of the afferent motor neuron of muscle fibers, thereby preventing contraction of muscle tissue associated with wrinkles and furrows.

Botox™ treatment is in high demand and thus, it is the goal of cosmetic scientists to develop a topical equivalency (see A. Blitzer et al., Arch. Otolaryngol. Head Neck Surg., 119, pages 1018 to 1022 (1993)) (see J. D. Carruthers et al., J. Dermatol. Surg. Oncol., 18, pages 17 to 21 (1992).

To meet consumer demand, many cosmetic compositions and cosmetic methods have been developed for skin care and treatment. However, many, if not most, of the products or treatment methods described to date lead to inadequate results or are marred by undesirable side effects. These may include irritation of the skin or adjacent mucous membranes, the production of excessive oiliness or greasiness of the skin or discoloration of the skin.

Dermal Repair: The regenerative ability of the dermis has a critical bearing on its ability to withstand the chronic muscle contraction and relaxation of the expressive muscles. As a consequence of aging or sun damaged skin, there is a reduction in the fibroblastic cells and blood vessels that are needed to rejuvenate the lower dermis. Fibroblasts in the "basal layer" of the upper dermis replicate into new cells more slowly, loose their capacity to manufacture collagen and are less able to organize and preserve the collagen fiber network. Since the dermal matrix is the source of collagen and major water holding molecules, i.e. the glycoaminoglycans and hyaluronic acid, preserving it is essential to the health of the epidermis. Without continual replenishment of precursor proteins, disorganization and dissolution of the collagen fiber network and the extra-cellular matrix, takes place. The result of this process is a flattening of the dermal-epidermal junction and a weakening of the mechanical resistance of the upper dermis. Thus, the aging skin has a much greater susceptibility for temporary deformations—that occur during facial expression—to become permanent, (see Oikarinen, "The Aging of Skin: Chronoaging Versus Photoaging," Photodermatol. Photoimmunol. Formation, Photomed., vol. 7, pp. 3-4, 1990), (see Thalmann et al. "A Computational Skin Model: Fold and Wrinkle Formation" pp. 1-5).

There are several teachings in the art (U.S. Pat. No. 6,794,362) (U.S. Pat. No. 6,777,389) that discuss singular molecules or compositions thereof for enhancing the elasticity of skin or strengthening the dermis. They are formulated from peptides or peptide-like compounds that mimic the molecular composition of elastin or add to it. Mitts et al. (U.S. Pat. No. 6,809,075) postulated that a peptide/retinoid composition, could integrate within the elastin component of the dermis, thereby increasing the ability of the skin to rebound from deformation. More often, the prior art teaches that natural or synthetic peptide formulations can enhance the collagen fiber network or extra-cellular substrate of the dermal matrix. Hence, a novel integrity (Lowe, N et al., "Pharmacology of Retinols In Skin", Vol. 3 (1989), pp. 240-248). However, the instability and irritation caused by retinoids are problematic. Approach advocated by Dioguardi (U.S. Pat. No. 5,198,465) is to increase the collagen content in the skin in general by the topical application of synthesized precursor collagen molecules and coenzymes of the collagen metabolic pathway. The premise is that direct replacement via diffusion and adsorption of precursor molecules fortifies deficient skin. A similar notion taught by Kludas (U.S. Pat. No. 5,055,298) is that a substantially natural composition can have a reparative and remodeling effect at the dermal-epidermal junction. Also, recent art (U.S. Pat. Nos. 6,906,036, 6,884,425) has taught that inhibitors of matrix metalloprotienases are capable of preventing the disruption of the dermis, healing it and facilitating a return to normal healthy skin. None of the aforementioned patents teach the capacity to stimulate fibroblastic activity and synthesis of collagen precursors; nor do they profess to restore dermal thickness and collagen fiber network.

In a recent patent, Varani et al. (U.S. Pat. No. 6,919,072) identifies a composition of a retinoid and a matrix metalloproteinase inhibitor that inhibits collagen breakdown, promotes collagen at the content by increasing procollagen synthesis, increases keratinocytes and fibroblastic proliferation. The invention restores the thickness of the epidermal-dermal interface in chronologically aged skin and it restores collagen content within the upper dermis to normal levels. Therein lies its property to give the skin strength to withstand environmental and physical stress. As with other retinoids, the retinoid of Lowe requires prolonged application and the dermal repair is much slower than with the preferred embodiment of this application.

The Significance of Peptides

The focus of the early art has been on disclosing substances that were thought to physically replenish the molecules that build new collagen or that add substances which irritate or disrupt the basal layer to effect its regeneration and healthy reconstitution. More recent art teaches the benefits of topical peptide treatments in stimulating the upper dermis to renew itself by cellular re-growth. This is supported by the knowledge that, the body has naturally occurring peptides that are instrumental in stimulating the healing process following a wound to the skin. Robinson teaches (U.S. Pat. No. 6,492,326) various formulations containing combinations of palmitoyl pentapeptide-3, derivatives of pentapeptides and mixtures thereof. Lintner (U.S. Pat. No. 6,620,419) discloses peptide formulas of the general sequence palmitoyl-lysyl-threonyl-threonyl-lysyl-serine (palmitoyl group attached to SEQ ID No. 1) that increase the synthesis of collagen and glylcosaminoglycans. They act synergistically to heal wrinkles and other forms of skin aging far more effectively than earlier formulations. The key difference in the Lintner teaching to that of Robinson is the addition of a fatty acid chain onto the terminal end of a pentapeptide that makes this lipophilic modified peptide very efficient at penetrating the epidermis and thus more effective in reaching the formative layers of the dermis. The net result is to increase the thickness of the skin by restoring the reparative capacity of the upper dermis. Consequently, the skin is better able to withstand the defoliation imposed on it by the active contraction and relaxation of expression muscles and microcontractions within the skin itself.

More comprehensive studies have found that environmental factors, such as stress, sun exposure and impurities in food, water and air also adversely affect components of the epidermal and dermal layers of the skin which, in turn, impact and alter the appearance of the skin and lead to an appearance of premature aging. For example, factors such as free radicals, reactive nitrogen species ("RNS"), reactive oxygen species ("ROS") and other oxidizing species ("OOS") can adversely impact the human body including the skin. Particular factors within the groups noted above that have been found to impact and adversely affect the appearance of the skin include nitric oxide, superoxide radicals, hydrogen peroxide and hydroxide free radicals. These factors have been variously implicated in a number of skin conditions including photodamage, general aging of the skin, contact dermatitis, wrinkling, lipid peroxidation, enzyme degradation, reduction and breakdown of collagen and or elastin, degradation and inhibited reproduction ofDMA, inflammation and general damage to the skin tissue.

Antioxidant activity is an activity that reduces production of reactive oxygen species in the body and at the same time, prevents oxidation that causes irrecoverable damages to cells. Ground-state or triplet oxygen can be activated as a result of exposure to environmental or biochemical factors such as enzymes, reduction metabolism, chemical compounds, pollutants and photochemical reactions, and transformed into reactive oxygen species (ROS) which have a high reactivity such as superoxide radicals, hydroxy radicals and hydrogen peroxide. Accordingly, it results in irreversibly disrupting cell constituents. The actions of such reactive oxygen species can be reduced by antioxidant enzymes such as superoxide dismutase (SOD), catalase and peroxidase and antioxidant substances such as vitamin C, vitamin E and glutathione, which all form the body's defense system. However, where disorder of such a defense mechanism in the body or exposure to excessive reactive oxygen species occurs, reactive oxygen species may irreversibly disrupt lipid, protein and DNA. Various diseases inclusive of aging, cancer, multiple arteriosclerosis, arthritis and Parkinson's disease are the result.

Synthetic antioxidants such as BHA (butylated hydroxy anisole), BHT (butylated hydroxy toluene) and NDGA (nor-dihydro-guaiaretic acid) have been developed to date. By way of examples of natural antioxidants, there are antioxidant enzymes such as superoxide dismutase, peroxidase, catalase and glutathione peroxidase; and non-enzymatic antioxidant substances such as tocopherol (vitamin E), ascorbic acid (vitamin C), carotenoid and glutathione.

However, synthetic antioxidants may cause allergic reactions and oncogenesis due to their strong toxicity in the body, and are easily disrupted by heat due to temperature sensitivity. On the other hand, natural antioxidants are safer than synthetic antioxidants in the body but have the problem of weaker effect. Therefore, the development of a new natural antioxidant having no problem with safety in use and also having excellent antioxidant activity is required. Topically-applied antioxidants do have merit for all skin types to keep skin healthy and help prevent sun damage and improve cell function.

Antioxidants have been conclusively shown to exert a positive effect on reducing skin irritation and inflammation, and that is a crucial step in creating or maintaining healthy, vibrant skin and, therefore potentially reducing wrinkles. (International Journal of Experimental Pathology, 2000:257-263; Skin Pharmacology and Applied Skin Physiology, 2000: 143-149)

Several hundred molecules having a polyphenol (polyhydroxyphenol) structure (i.e. several hydroxyl groups on aromatic rings) have been identified in edible plants. These molecules are secondary metabolites of plants and are generally involved in defense against ultraviolet radiation or aggression by pathogens. Polyphenols are widespread constituents of fruits, vegetables, cereals, dry legumes, chocolate, and beverages such as tea, coffee or wine.

These compounds may be classified into different groups as a function of the number of phenol rings that they contain and of the structural elements that bind these rings to one another. Classes of polyphenols include the phenolic acids, flavonoids, stilbenes and lignans. There are two classes of phenolic acids: derivatives of benzoic acid and derivatives of cinnamic acid.

It is indeed not practical to measure each and every one of the antioxidants in vivo. It is also now widely hypothesized that the major factor influencing oxidative stress is the overall antioxidant status of the system, which prevents diseases by eliminating free radicals and ROS. Therefore, it is essential to have a method capable of measuring collectively the extracellular antioxidant status. There are methods for measuring antioxidant status which are based on the inhibition of generated free radicals reaching the target indicator molecules, by antioxidants. The common feature for inhibition assays is to generate a free radical to react with a target molecule, thereby generating an endpoint that can be observed and quantified. Addition of antioxidants inhibits the development of this endpoint. A good example of this is the DPPH (1,1-diphenyl-2-hydrazyl) free radical scavenging activity.

Elastin, found in highest concentrations in the elastic fibers of connective tissues, is responsible for the texture and tone of the skin. ELASTASE, a serine protease enzyme, has a role in dissociating tissues which contain extensive intercellular fiber networks. Excess elastase production will result in wrinkling of skin/premature ageing.

The vital protein, collagen, maintains the skin tone and structure. COLLAGENASE is a serine protease enzyme that cleans the wound of any dead tissue leaving the wound bed ready for healing. Collagenase, intensely produced during inflammation, is known to have role in Skin wrinkling by digesting the vital protein collagen that maintains the skin tone and structure.

Another mechanism for Anti ageing is collagen enhancement in the skin. Actives that can physically replenish the molecules that build new collagen or that adds substances which irritate or disrupt the basal layer to effect its regeneration and healthy reconstitution are excellent for Anti-ageing compositions. More recent art teaches the benefits of topical peptide treatments in stimulating the upper dermis to renew itself by cellular re-growth. This is supported by the knowledge that the body has naturally occurring peptides that are instrumental in stimulating the healing process following a wound to the skin. Robinson teaches (U.S. Pat. No. 6,492,326) various formulations containing palmitoyl pentapeptide-3, derivatives of pentapeptides, and mixtures thereof. Lintner (U.S. Pat. No. 6,620,419) discloses peptide formulas of the general sequence palmitoyl-lysyl-threonyl-lysyl-serine (Palmitoyl group attached to SEQ ID No. 1) that increase the synthesis of collagen and glylcosaminoglycans. They act synergistically to heal wrinkles and other forms of skin aging far more effectively than earlier formulations.

The present invention discloses composition containing peptide of SEQ ID No. 1 linked to oleanolic acid and its effective use in a method of skin repair and firming by the regulation of associated gene expression.

Accordingly, it is the principle objective of the present invention to disclose a method of skin repair and firming, said method comprising the step of bringing into contact a pentapeptide conjugate of oleanolic acid with skin cells so that the effect of increased cellular communication at the molecular level to bring about gene and protein expression in the cells of the skin that enable repair and firming is realized.

The present invention fulfills the aforesaid objective and provides further related advantages.

SUMMARY OF THE INVENTION

Disclosed is the a method of skin repair and firming, said method comprising the step of bringing into contact a pentapeptide conjugate of oleanolic acid with skin cells so that the effect of increased cellular communication at the molecular level to bring about gene and protein expression in the cells of the skin that enable repair and firming is realized. The invention demonstrates the effect of the pentapeptide conjugate of oleanolic acid in increasing Transforming Growth Factor-β and Fibroblast Growth Factor gene expressions in the skin.

Other features and advantages of the present invention will become apparent from the following more detailed description, taken in conjunction with the accompanying drawings, which illustrate, by way of example, the principle of the invention.

DETAILED DESCRIPTION OF THE MOST PREFERRED EMBODIMENTS (FIGS. 1-6)

In the most preferred embodiments, the present invention relates to the method of increasing the expression of Transforming Growth Factor-β in human fibroblasts, said method comprising step of bringing into contact human fibroblast cells with effective concentration of the composition containing peptide of SEQ ID No. 1 linked to oleanolic acid represented by STR#1 to bring about the regulation of extracellular matrix protein, in particular collagen synthesis.

In another most preferred embodiment, the present invention relates to the method of increasing the expression of Fibroblast Growth Factor in human fibroblasts, said method comprising step of bringing into contact human fibroblast cells with effective concentration of the composition containing peptide of SEQ ID No. 1 linked to oleanolic acid represented by STR#1 to bring about the effect of reduced skin scarring.

In yet other most preferred embodiments, the present invention also relates to,

A. A method of increasing the expression of HSP 90 gene in human skin, said method comprising step of bringing into contact human skin (treating human skin) with effective concentration of the composition containing peptide of SEQ ID No. 1 linked to oleanolic acid represented by STR#1 to bring about the effect of collagen repair and rebuilding.

B. A method of increasing the expression of HSP 47 gene in human skin, said method comprising step of bringing into contact human skin (treating human skin) with effective concentration of the composition containing peptide of SEQ ID No. 1 linked to oleanolic acid represented by STR#1 to bring about the effect of processing pro-collagen synthesis.

C. A method of increasing the expression of LOX (Lysyl oxidase) gene in human skin, said method comprising step of bringing into contact human skin (treating human skin) with effective concentration of the composition containing peptide of SEQ ID No. 1 linked to oleanolic acid represented by STR#1 to being about the effect of extracellular matrix remodelling.

D. A method of increasing the expression of tissue inhibitors of matrix metalloproteinases (TIMP) gene in human skin, said method comprising step of bringing into contact human skin (treating human skin) with effective concentration of the composition containing peptide of SEQ ID No. 1 linked to oleanolic acid represented by STR#1 to bring about the inhibition of matrix metalloproteinases like collagenase and elastase.

In further exemplary embodiments, the present invention also relates to,

A. A method of increasing the expression of genes improving barrier function of skin selected from group consisting of cornodesmosin (CDSN), claudin 7 (CLDN7), filaggrin (FLG), Late Cornified Envelope 3D (LCE3D), loricrin (LOR) and integrin beta 4 (ITGB4), said method comprising step of bringing into contact human skin (treating human skin) with effective concentration of the composition containing peptide of SEQ ID No. 1 linked to oleanolic acid represented by STR#1.

B. A method of increasing the expression of genes increasing keratinocyte differentiation in human skin selected from group consisting of loricrin (LOR) and calmodulin like 5 (CALML5), said method comprising step of bringing into contact human skin (treating human skin) with effective concentration of the composition containing peptide of SEQ ID No. 1 linked to oleanolic acid represented by STR#1.

C. A method of increasing the expression of genes improving cell cycle and cell proliferation in skin selected from group consisting of peroxisome proliferator-activated receptor (PPARD), tumor protein p63 (TP63) and antigen identified by Ki-67 antibody (MKI67), said method comprising step of bringing into contact human skin (treating human skin) with effective concentration of the composition containing peptide of SEQ ID No. 1 linked to oleanolic acid represented by STR#1.

D. A method of increasing skin hydration by increasing the expression of aquaporin5 gene (AQP5) in skin, said method comprising step of bringing into contact human skin (treating human skin) with effective concentration of the composition containing peptide of SEQ ID No. 1 linked to oleanolic acid represented by STR#1.

E. A method of increasing collagen synthesis in skin by increasing the expression of associated transforming growth factor-beta 1 (TGFB1) gene in skin, said method comprising step of bringing into contact human skin (treating human skin) with effective concentration of the composition containing peptide of SEQ ID No. 1 linked to oleanolic acid represented by STR#1.

F. A method of inducing melanogenesis in skin by increasing the expression of associated bone morphogenetic protein 2 (BMP2) gene in skin, said method comprising step of bringing into contact human skin (treating human skin) with effective concentration of the composition containing peptide of SEQ ID No. 1 linked to oleanolic acid represented by STR#1.

lation/building ability of test composition containing peptide of SEQ ID No. 1 linked to oleanolic acid represented by STR#1.

(STR#1)

To further elucidate the most preferred embodiments of the present invention, the following illustrative examples are included herewith.

EXAMPLE 1

Evaluation of Transforming Growth Factor Beta (TGF-β) and Fibroblast Growth Factor (FGF):

Human Dermal Fibroblast (HDF) cells were cultured in DMEM medium with 10% FBS and seeded in 96 well tissue culture plate for the test. 24 hrs post seeding, HDF were treated with the test sample (composition containing peptide of SEQ ID No. 1 linked to oleanolic acid represented by STR#1) at graded concentrations and incubated for 48 hrs in 5% $CO_2$ incubator at 37° C. After 48 hrs the supernatant was collected from each well. The amount of TGF-β and FGF produced by the various treated HDF was quantified using ELISA method according to the kit protocol provided by the manufacturer (R&D Systems) and absorbance was measured at 450 nm using Fluostar Optima. Standard curve was generated by plotting absorbance values of standards against appropriate TGF-β/FGF concentrations TGF-β/FGF concentrations of the control and test samples were calculated from the standard graph equation. Percentage increase of expression in test samples was calculated with respect to un-treated cells. The results of the experiment are exemplified in FIGS. 1 and 2 respectively. The importance of TGF-β1 in the synthesis of extracellular matrix in well established in 1. Yang T et al, "miR-29 mediates TGFβ1-induced extracellular matrix synthesis through activation of P13K-AKT pathway in human lung fibroblasts", J Cell Biochem. 2013 June; 114(6):1336-42;
2. Tan J et al, "MicroRNA-29 mediates TGFβ1-induced extracellular matrix synthesis by targeting wnt/β-catenin pathway in human orbital fibroblasts." Int J Clin Exp Pathol. 2014 Oct. 15; 7(11):7571-7;
3. Das D et al, "TGF-beta1-Induced MARK activation promotes collagen synthesis, nodule formation, redox stress and cellular senescence in porcine aortic valve interstitial cells.", J Heart Valve Dis. 2013 September; 22(5):621-30.

Figure 1:
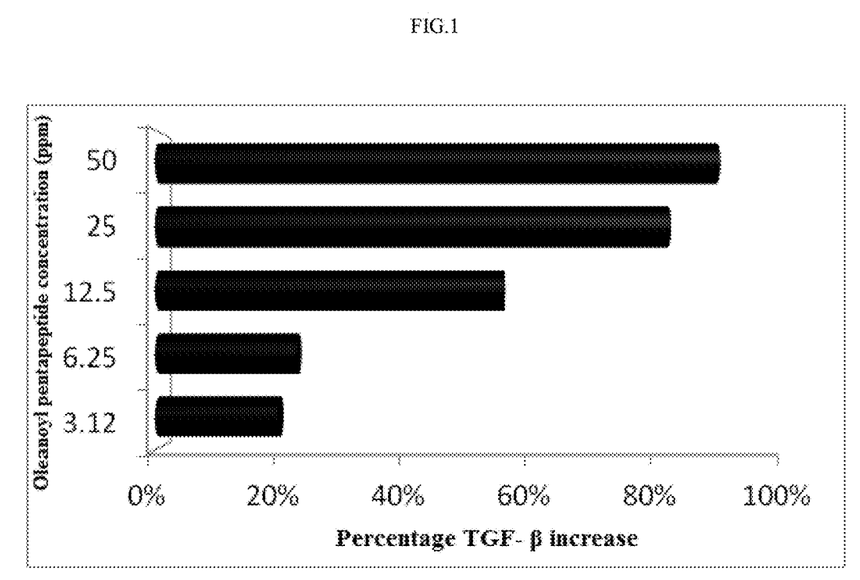
FIG. 1 shows the graphical representation of percentage increase in Transforming Growth Factor-β (TGF-β) expression in Human Dermal Fibroblast (HDF) cells following exposure to varying concentrations of the composition containing peptide of SEQ ID No. 1 linked to oleanolic acid.
Figure 2:
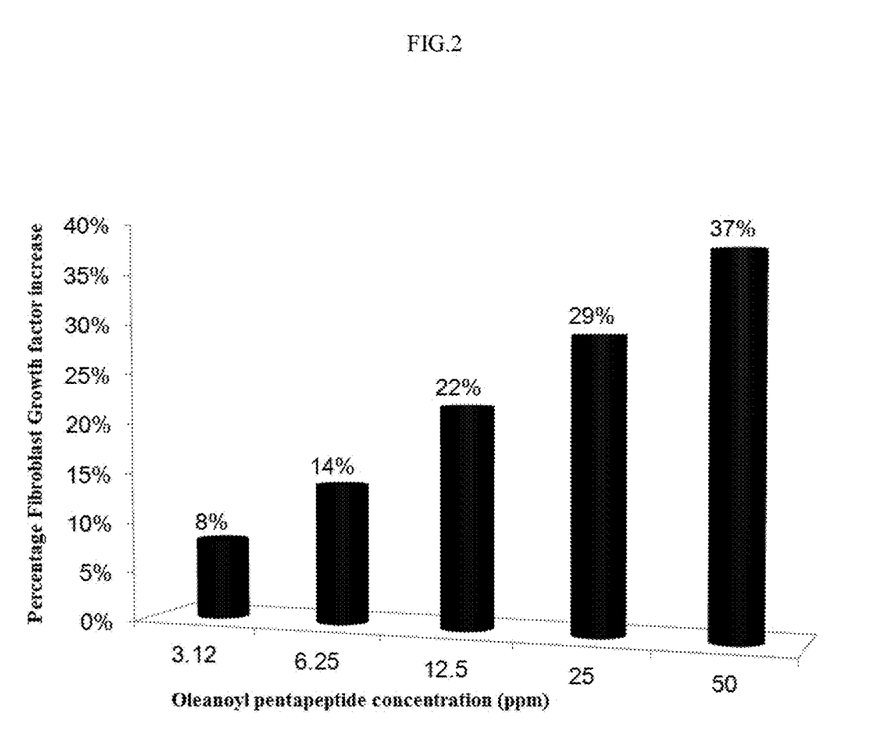
FIG. 2 shows the graphical representation of percentage increase in Fibroblast Growth Factor expression in Human Dermal Fibroblast (HDF) cells following exposure to varying concentrations of the composition containing peptide of SEQ ID No. 1 linked to oleanolic acid.

The increase in TGF-β expression in human dermal fibroblasts in thus clearly indicative of the collagen stimu- Similarity, the ability of fibroblasts and myofibroblasts in would healing has been documented in Ian. A. Derby, "Fibroblasts and myofibroblasts in wound healing", Clin Cosmet Investig Dermatol. 2014; 7: 301-311. The importance on the fibroblast growth factor and its bioavailability in the skin tissue microenviron to coordinate with myofibroblasts to maintain skin homeostasis and physiological tissue repair including scarring has been discussed in the aforementioned reference. The increase in fibroblast growth factor expression in human dermal fibroblasts in thus clearly indicative of physiological tissue repair ability of test composition containing peptide of SEQ ID No. 1 linked to oleanolic acid represented by STR#1.

EXAMPLE 2

Gene Expression Analysis:

The objective of the study was to understand how application of test composition containing peptide of SEQ ID No. 1 linked to oleanolic acid represented by STR#1 influences gene expression in the skin. The current study was conducted using a full-thickness in vitro skin culture model (EFT-400, MatTek). One hundred microliters of Test Material was applied to the surface of each test culture and incubated for a period of 24 hours.

Treatment and Maintenance of cultures: 100 μL of test composition containing peptide of SEQ ID No. 1 linked to oleanolic acid represented by STR#1 was applied to the center of each EFT-400 culture. A sterile glass spreader was used to distribute the Test Material. Each culture was visually inspected to ensure even distribution. Following application, the cultures were returned to the incubator at 37° C. with 5% CO2 for 24 hours. After 24 hours, the Test Materials were washed from the surface of each culture with sterile PBS. Following removal of test material, each culture was cut into quarters and placed into RNA solution.

RNA Isolation: RNA was isolated from tissues using a Maxwell 16 LEV RNA Tissue kit following the manufacturer's instructions (Promega) and vacuum concentrated until >200 ng/uL as required for OpenArray processing. RNA concentration and purity were determined using a Nanodrop 2000 spectrophotometer. cDNA synthesis: cDNA was generated using a High Capacity cDNA Synthesis Kit according to the manufacturer's instructions for OpenArray processing (Life Technologies).

qPCR Processing: qPCR reactions were run using validated Taqman gene expression assays in an OpenArray format. OpenArrays were run in a Life Technologies QuantStudio 12K Flex instrument.

Data Analysis: qPCR data was imported into RealTime StatMiner software v4.2 for statistical analysis using the relative quantitation (RQ) method. In the first step of an RQ analysis, the CT value of the target gene is normalized to the CT value of an endogenous control gene for each sample to generate the delta CT (dCT).

FIGS. 3, 4, 5 and 6 show the percentage increase in the skin expressions of the following genes following the application of test composition containing peptide of SEQ ID No. 1 linked to oleanolic acid represented by STR#1. The gene expression and their associated benefits on skin health have been highlighted below. Up-regulation of respective gene expressions in the skin following application of test composition containing peptide of SEQ ID No. 1 point directly to realizing the gene expression associated skin health benefits.

Figure 3:
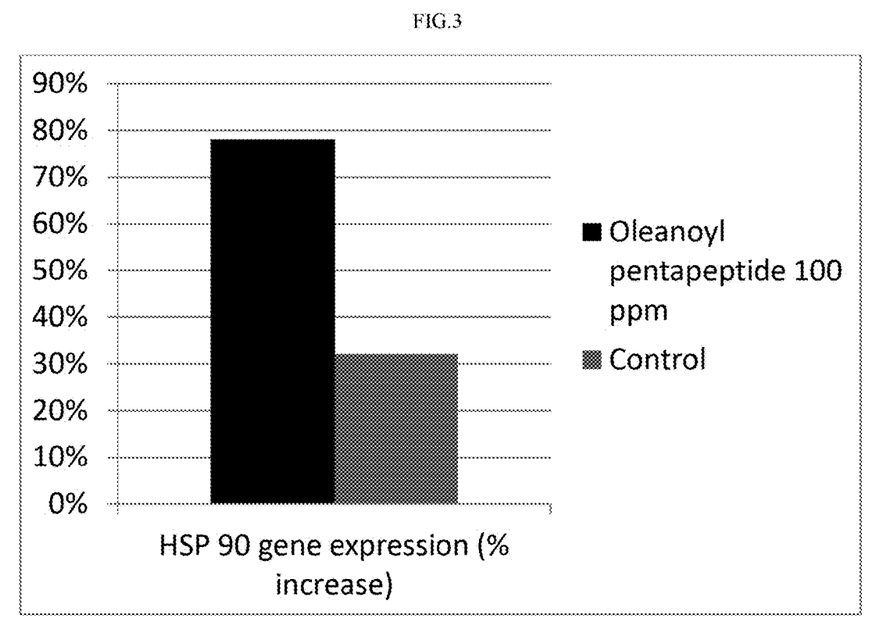
FIG. 3 shows the percentage increase in the expression of HSP 90 gene in skin following exposure to varying concentrations of the composition containing peptide of SEQ ID No. 1 linked to oleanolic acid.
Figure 5:
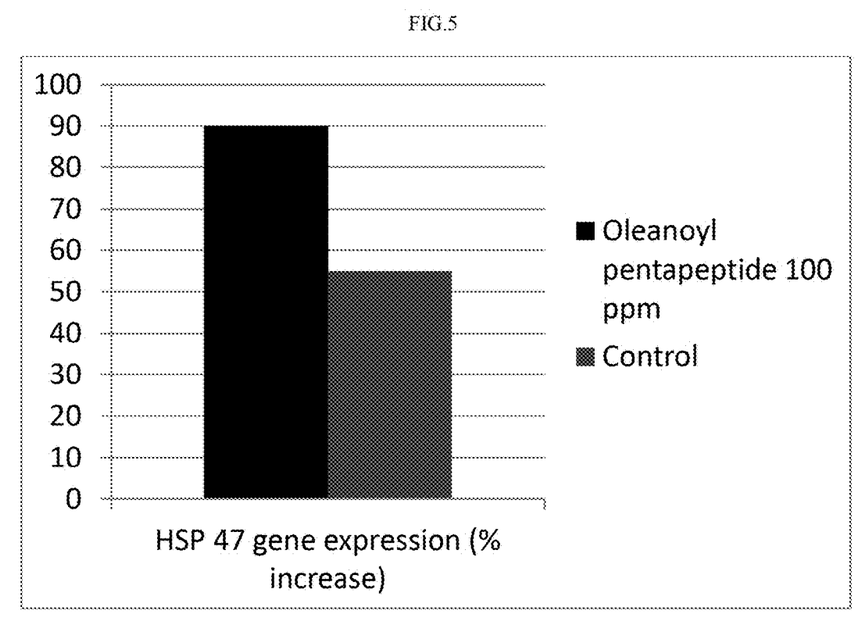
FIG. 5 shows the percentage increase in the expression of HSP-47 gene in skin following exposure to varying concentrations of the composition containing peptide of SEQ ID No. 1 linked to oleanolic acid.

1. HSP-90 (helps in DNA repair and extracellular matrix remodeling-Radovanac K et al, "Stabilization of integrin-linked kinase by the Hsp90-CHIP axis impacts cellular force generation, migration and the fibrotic response.", *EMBO J.* 2013 May 15; 32(10):1409-24);

2. HSP-47 facts as a molecular chaperone facilitating the folding and assembly of procollagen molecules, retaining unfolded molecules within the ER, and assisting the transport of correctly folded molecules from the ER to the Golgi apparatus-Mohammed Tasab et al, "Hsp47: a molecular chaperone that interacts with and stabilizes correctly-folded procollagen", EMBO J. May 15, 2000; 19(10): 2204-2211)

Figure 4:
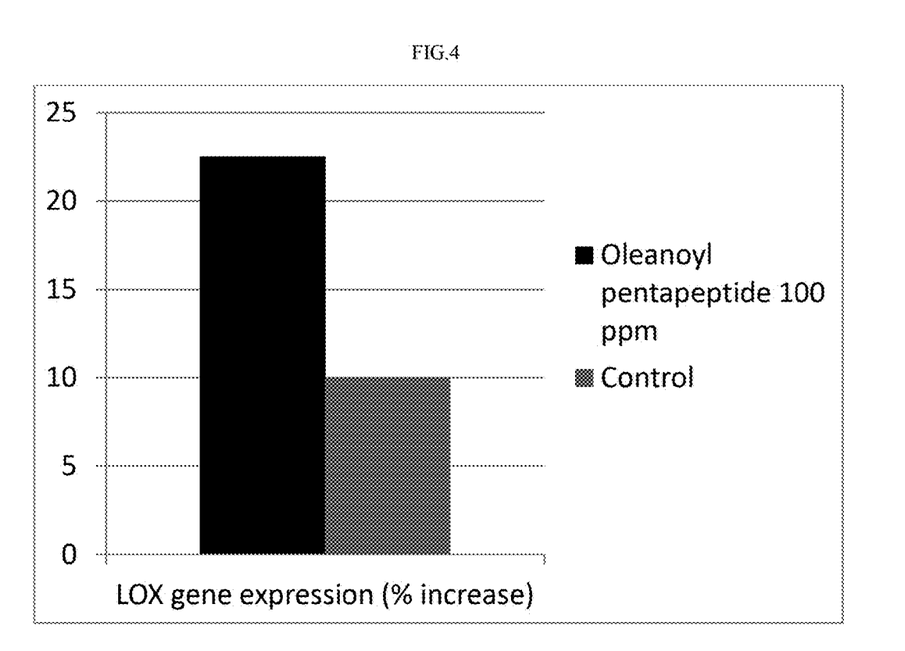
FIG. 4 shows the percentage increase in the expression of LOX gene in skin following exposure to varying concentrations of the composition containing peptide of SEQ ID No. 1 linked to oleanolic acid.
Figure 6:
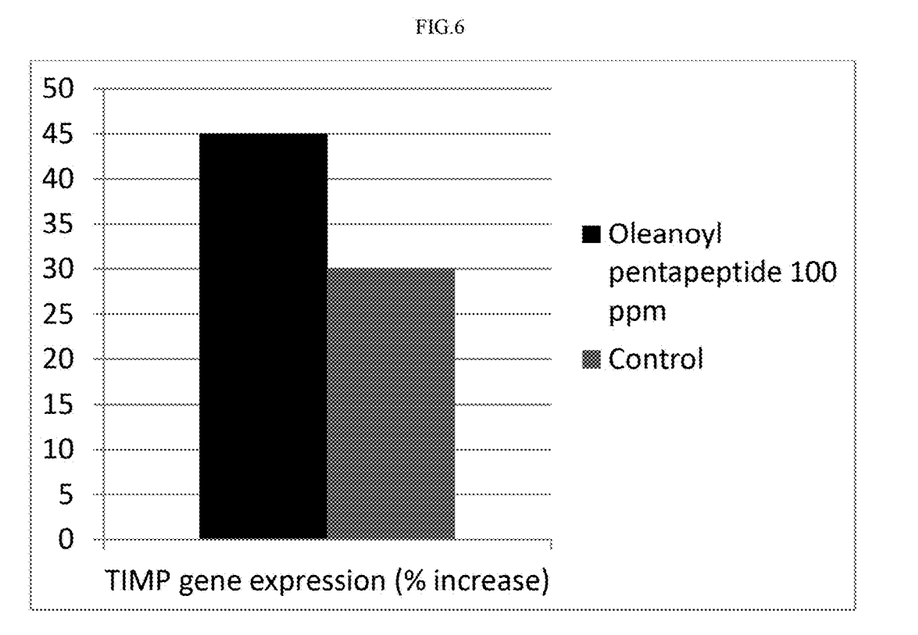
FIG. 6 shows the percentage increase in the expression of TIMP gene in skin following exposure to varying concentrations of the composition containing peptide of SEQ ID No. 1 linked to oleanolic acid.

3. LOX (helps extracellular matrix protein cross-linking-Rucker RB et al, "Copper, lysyl oxidase, and extracellular matrix protein cross-linking", Am J Clin Nutr. 1998 May; 67(5 Suppl):996S-1002S) and 4. TIMP (Tissue inhibitors of matrix metalloproteinases control matrix metalloproteinase activity and minimize matrix degeneration-Dimitra Bourboulia et al. "Matrix MetalloProteinases (MMPs) and Tissue Inhibitors of MetalloProteinases (TIMPs): positive and negative regulators intumor cell adhesion", Semin Cancer Biol. June 2010; 20(3): 161-168)

The up-regulation of other important genes by test composition containing peptide of SEQ ID No. 1 is represented in Table 1. Such up-regulation directly points to the ability of test composition containing peptide of SeQ ID No. 1 to bring about the known gene functions in fostering various aspects of skin health (homeostasis, integrity and function)

TABLE 1

| Gene | Gene Name | Fold Increase | Gene Function |
|---|---|---|---|
| CDSN | corneodesmosin | 1.78 | Barrier function |
| CLDN7 | claudin 7 | 1.69 | Barrier function |

TABLE 1-continued

| Gene | Gene Name | Fold Increase | Gene Function |
|---|---|---|---|
| FLG | filaggrin | 2.23 | Barrier function |
| LCE3D | late cornified envelope 3D | 1.61 | Barrier function |
| LOR | loricrin | 1.63 | Barrier/Keratinocyte differentiation |
| ITGB4 | integrin, beta 4 | 1.76 | Cell adhesion/Barrier function |
| PPARD | peroxisome proliferator-activated receptor | 1.59 | Cell cycle/cell proliferation |
| TP63 | tumor protein p63 | 1.56 | Cell cycle/cell proliferation |
| MKI67 | antigen identified by Ki-67 antibody | 1.83 | Cell proliferation |
| KLK5 | kallikrein-related peptidase 5 | 2.44 | Desquamation/Extracellular matrix |
| TGFB1 | transforming growth factor, beta 1 | 1.72 | Extracellular matrix/Collagen synthesis |
| DSG3 | desmoglein 3 | 2.19 | Extracellular matrix/Cell adhesion |
| AQP5 | aquaporin 5 | 1.97 | Hydration |
| CALML5 | calmodulin-like 5 | 1.91 | Keratinocyte differentiation |
| BMP2 | bone morphogenetic protein 2 | 1.80 | Whitening/Melanogenesis |

The down-regulation of other important genes by test composition containing peptide of SEQ ID No. 1 is represented in Table II. Such down-regulation directly points to the ability of test composition containing peptide of SEQ ID No. 1 to bring down the effects of the known gene functions thereby fostering optimal skin health.

TABLE II

| Gene | Gene Name | Fold Decrease | Gene Function |
|---|---|---|---|
| IL1A | interleukin 1, alpha | −1.77 | Inflammatory response |
| IL8 | interleukin 8 | −1.68 | Inflammatory response |
| PTGS2 | Prostaglandin endoperoxide synthase 2/COX2 | −1.80 | Inflammatory response |
| TNF | tumor necrosis factor (TNFsuperfamily, member) | −4.34 | Inflammatory response/ |
| KRT10 | keratin 10 | −1.71 | Keratinocyte differentiation |
| KRT4 | keratin 4 | −2.11 | Keratinocyte differentiation |

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of maintaining water homeostasis in hydration deficient human skin, characterized by skin discontinuities by increasing the selective expression of water channel protein aquaporin 5 (AQP 5) in areas of skin prone to such expression to bring about the effect of AQP5 mediated water transport therein, said method comprising step of bringing into contact areas of skin prone to such AQP5 expression and an effective concentration of composition containing peptide of SEQ ID NO: 1 linked to oleanolic acid represented by STR#1

(STR#1)

2. A method of increasing the expression of genes and associated proteins capable of improving skin barrier function in areas of skin with discontinuities to prevent water evaporation from areas of skin prone to such expression wherein said genes and associated proteins are selected from the group consisting of corneodesmosin (CDSN), claudin 7 (CLDN7), filaggrin (FLG), Late Cornified Envelope 3D (LCE3D), loricrin (LOR) and integrin beta 4 (ITGB4), said method comprising step of bringing into contact areas of skin prone to such gene expression with effective concentration of composition containing peptide of SEQ ID NO: 1 linked to oleanolic acid represented by STR#1

3. A method of increasing the expression of genes and associated proteins capable of increasing keratinocyte differentiation in human skin, characterized by skin discontinuities to bring about the effect of preventing water evaporation from areas of human skin prone to such expression, wherein said genes and proteins are selected from group consisting of loricrin (LOR) and calmodulin like 5 (CALML5), said method comprising step of bringing into contact areas of human skin prone to such expression with effective concentration of composition containing peptide of SEQ ID NO: 1 linked to oleanolic acid represented by STR#1

* * * * *